US010865468B2

(12) United States Patent
Walker

(10) Patent No.: US 10,865,468 B2
(45) Date of Patent: Dec. 15, 2020

(54) METHODS OF FORMING AN OXIDE LAYER ON A METAL BODY

(71) Applicant: VIPER TECHNOLOGIES LLC, Portland, OR (US)

(72) Inventor: David L. Walker, Portland, OR (US)

(73) Assignee: Avalign Technologies, Inc., Bannockburn, IL (US)

( * ) Notice: Subject to any disclaimer, the term of this patent is extended or adjusted under 35 U.S.C. 154(b) by 739 days.

(21) Appl. No.: 15/195,624

(22) Filed: Jun. 28, 2016

(65) Prior Publication Data

US 2016/0305005 A1    Oct. 20, 2016

Related U.S. Application Data

(63) Continuation-in-part of application No. 14/061,466, filed on Oct. 23, 2013, now Pat. No. 9,404,173.

(51) Int. Cl.
| C23C 8/10 | (2006.01) |
| B28B 5/00 | (2006.01) |
| A61F 2/00 | (2006.01) |
| C23C 8/02 | (2006.01) |
| C23C 8/80 | (2006.01) |
| C22F 1/18 | (2006.01) |
| B22F 3/04 | (2006.01) |
| B24B 31/06 | (2006.01) |
| A61F 2/36 | (2006.01) |
| A61F 2/38 | (2006.01) |
| A61F 2/30 | (2006.01) |
| B28B 11/00 | (2006.01) |

(52) U.S. Cl.
CPC .............. *C23C 8/10* (2013.01); *A61F 2/0077* (2013.01); *A61F 2/30767* (2013.01); *A61F 2/3609* (2013.01); *A61F 2/3859* (2013.01); *B22F 3/04* (2013.01); *B24B 31/06* (2013.01); *C22F 1/186* (2013.01); *C23C 8/02* (2013.01); *C23C 8/80* (2013.01); *A61F 2002/30084* (2013.01); *A61F 2002/30107* (2013.01); *A61F 2240/001* (2013.01)

(58) Field of Classification Search
CPC ....... C23C 8/10–18; A61F 2002/30084; A61F 2002/30107; A61F 2/0077; A61F 2/30767; A61F 2/3609; A61F 2/3859
See application file for complete search history.

(56) References Cited

U.S. PATENT DOCUMENTS

| 3,805,459 | A | 4/1974 | Baksay |
| 5,900,083 | A | 5/1999 | Reed et al. |
| 2002/0042656 | A1 | 4/2002 | Hunter et al. |
| 2006/0285991 | A1 | 12/2006 | McKinley |

(Continued)

OTHER PUBLICATIONS

EPO Search Report dated Jan. 28, 2020 for European Patent Application No. 17821152.0.

*Primary Examiner* — Lois L Zheng
(74) *Attorney, Agent, or Firm* — BakerHostetler

(57) ABSTRACT

In one embodiment, a Metal Injection Molded (MIM) body may have one or more surfaces comprising a zirconium alloy. A method of forming an oxide layer on the zirconium alloy surface(s) of the MIM body may include hot isostatic pressing the MIM body, heat treating the MIM body, machining the MIM body to desired shape dimensions, polishing the surface of the MIM body, and oxidizing the polished surface of the MIM body. In some embodiments, the polishing step may include a first vibratory finishing step; and a second vibratory finishing step.

17 Claims, 5 Drawing Sheets

(56) References Cited

U.S. PATENT DOCUMENTS

2011/0015756 A1   1/2011  Pawar et al.
2012/0136400 A1   5/2012  Julien et al.
2015/0107721 A1   4/2015  Walker

METHODS OF FORMING AN OXIDE LAYER ON A METAL BODY

BACKGROUND

The present disclosure relates generally to methods for forming an oxide layer on metal bodies. In particular, methods of forming an oxide layer on a zirconium alloy surface of a metal body are described.

Known methods of producing zirconium alloy based medical implants are not entirely satisfactory for the range of applications in which they are employed. Zirconium alloys, and Zirconium-2.5 Niobium in particular, has been used to in medical implants for weight bearing components, such as femoral heads and knee replacement femoral components. One benefit of using zirconium alloy is that an oxidation process can be readily applied to create a substantially dense, smooth, and uniform layer of zirconium oxide, which defines a low friction coefficient and is exceptionally hard.

An oxidation layer provides numerous operational benefits, such as superior resistance to wear and corrosion. These specific benefits are particularly relevant in the medical implant industry because malfunctioning implants could cause bodily injury or require invasive surgery to repair. The low friction coefficient of oxide layers tend to reduce wear when the oxide surfaces articulate against relatively soft materials, such as plastic implants paired with metal implants.

Both cast and forged zirconium alloy based medical implants can meet relevant American Society for Testing and Materials International ("ASTM") chemical and mechanical requirements for medical implants. Cast alloy parts, however, are significantly cheaper to manufacture than forged analogues. Cast alloy parts, prior to many of the innovations described in this disclosure, have historically produced lower quality products, however.

For example, many cast zirconium alloy parts have had unsatisfactory surface conditions to enable zirconium oxide layers to a desired extent. For example, many cast zirconium alloy products define large, visible grain boundaries, which often result in uneven and cracked zirconium oxide layers when the products are oxidized. Further, these imperfections often result in a product that visually appears unreliable, which may lower medical practitioners' confidence in them.

Each of these limitations of conventional zirconium alloy casting processes result in lower quality products. The lower quality products typically have less dense, smooth, and uniform surfaces and lack the resistance to corrosion and wear of forged products. As a result, conventional zirconium alloy parts are not cost-effective, suitable replacements for forged zirconium alloy parts.

Thus, there exists a need for processes for producing zirconium alloy products that that improve upon and advance the design of known methods. In particular, the field requires methods to increase the quality of the zirconium oxide layer of metal bodies to be used, for example, as medical implants. Even more particularly, there exists a need for methods of preparing the surface of cast zirconium alloy products with improved surface characteristics prior to creating the oxidized layer. Furthermore, there exists a need for methods of producing a zirconium oxide layer on metal bodies produced by methods other than casting.

It would be desirable to increase the quality of the oxidized layer of products having a zirconium-containing surface. Such products may be cost-effective and suitable replacement of, for example, forged zirconium alloy products. Indeed, it would be desirable to produce high-quality zirconium alloy products at a significantly lower price than conventional forged products. Examples of and useful methods relevant to increasing the quality of such zirconium-containing products are described below.

SUMMARY

In one embodiment, a Metal Injection Molded (MIM) body may have one or more surfaces comprising a zirconium alloy. A method of forming an oxide layer on the zirconium alloy surface(s) of the MIM body may include hot isostatic pressing the MIM body, heat treating the MIM body, machining the MIM body to desired shape dimensions, polishing the surface of the MIM body, and oxidizing the polished surface of the MIM body. In some embodiments, the polishing step may include a first vibratory finishing step; and a second vibratory finishing step.

In another embodiment, a method of producing a oxide layer on metal product may include preparing a surface of a cast zirconium alloy substrate for oxidation, hot isostatic pressing a cast substrate of near shape dimensions, heating the cast substrate, machining the cast substrate to desired shape dimensions, and treating the surface of the cast substrate to accept an oxide layer. In some examples, treating the surface of the cast substrate may include polishing the surface, peening the polished surface, and finishing the peened surface. Additional or alternative examples may include heat treating a cast substrate of near shape dimensions to define a homogenized grain structure within the cast substrate, machining the heat treated cast substrate to desired shape dimensions, and surface treating the machined cast substrate to modify its structure to define a recrystallized modified grain structure defining a reduced grain boundary size.

DETAILED DESCRIPTION

The disclosed methods will become better understood through review of the following detailed description in conjunction with the figures. The detailed description and figures provide mere examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described ire the following detailed description.

Throughout the following detailed description, examples of various methods are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Figure 1:
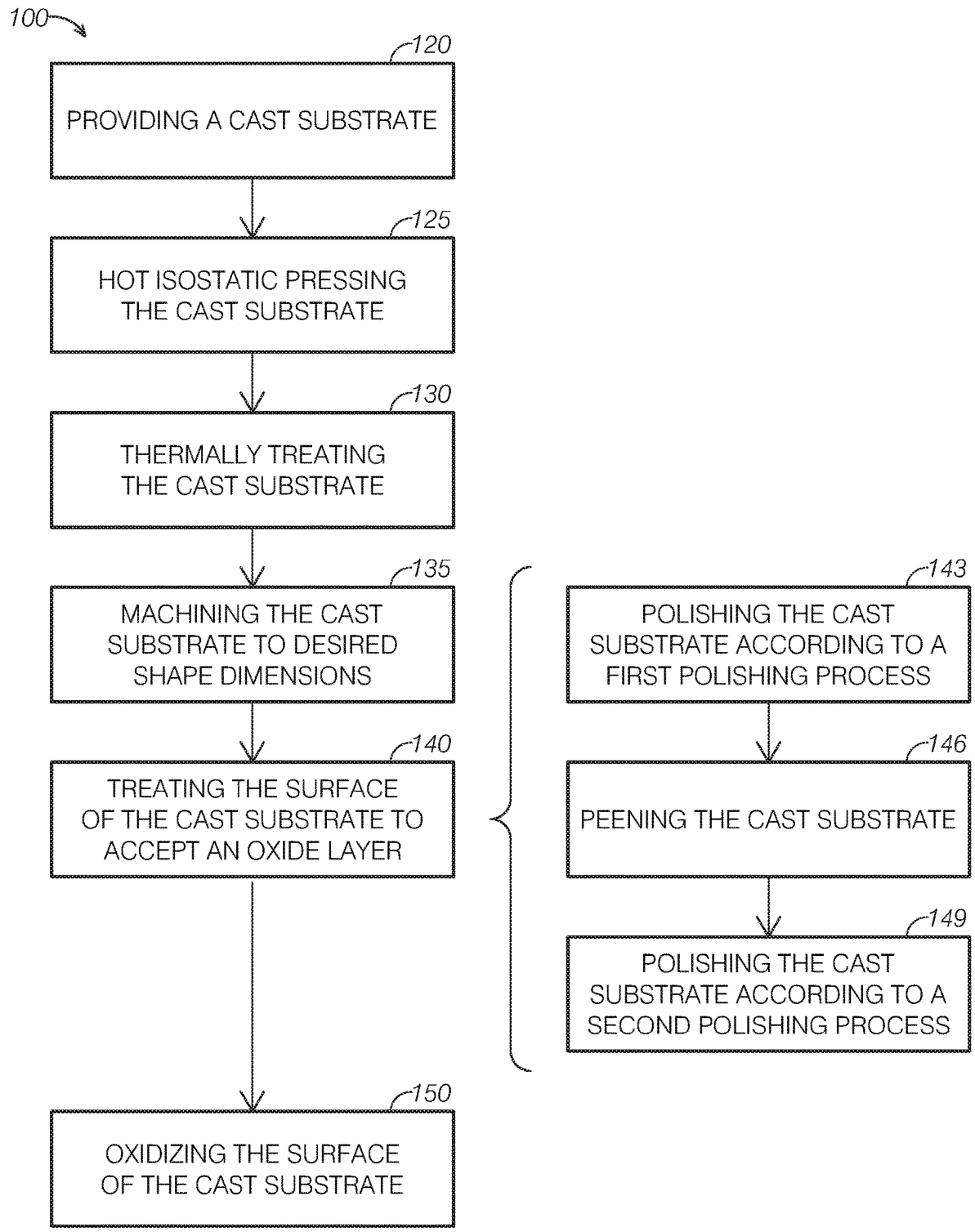
FIG. 1 is a flow diagram depicting a first example of a method of forming an oxidized surface on a cast zirconium alloy substrate.

With reference to FIG. 1, a first example of a method for preparing a surface of a cast zirconium alloy substrate for oxidation and oxidizing the surface of said substrate, method 100, will now be described. Method 100 includes providing a cast substrate at step 120, hot isostatic pressing the cast substrate at step 125, thermally treating the cast substrate at step 130, machining the cast substrate to desired shape dimensions at step 135, treating the surface of the cast substrate to accept an oxide layer at step 140, and oxidizing the surface of the cast substrate at step 150.

Method 100 and other disclosed methods overcome many of the shortcomings of conventional processes of producing zirconium alloy products. In particular, method 100 improves the oxide layers of cast zirconium oxide parts such that they may serve as cost-effective alternatives to their forged analogues. These improvements are accomplished, for example, through a series of steps that modify the surface microstructure of cast parts to encourage the surface to accept a satisfactory oxide layer.

The steps to modify the surface microstructure may include a series of heat treating, pressure treating, and surface finishing steps. These steps, collectively and individually, may reduce surface imperfections such as wide, visible grain boundaries or irregular or coarse surface characteristics. By repairing these imperfections on cast parts, these steps may, when applied, encourage cast parts to accept more satisfactory oxide layers than untreated cast parts. Further, some examples may result in oxidized cast parts with a desired aesthetic blue-black or black appearance free of visible gain boundaries, as is often found on oxidized zirconium-2.5 niobium forgings.

The improved surface characteristics, such as grain size and smoothness, of cast parts produced from method 100 encourage the casts to more satisfactorily accept zirconium oxide layers at step 150. The resulting layers may be more dense, smooth, and uniform than those accepted by many conventional cast parts. By using the disclosed methods, cast parts may serve as a cost-effective alternative to forged analogues in providing near-shape, ASTM-compliant zirconium oxide parts for medical implants.

The disclosed methods may be particularly suited to prosthetic implants, such as femoral knees and hips. For example, FIGS. 2-6 show two examples of prosthetic implants have been treated and oxidized by methods disclosed herein to produce a satisfactory zirconium oxine layer femoral head 160 and femoral knee 180. Because these illustrated examples have been treated and oxidized according to the method steps described in detail below, they include a femoral head oxidized layer 164 and a femoral knee oxidized layer 184. The untreated and oxidized cast parts, or substrates, would be similar in shape and size, but lack the associated oxidized layer.

While this disclosure considers, as examples, cast parts specifically used for medical implants, the disclosed methods have widespread applicability to any use of zirconium oxide alloy parts. In particular, the methods described below may be used with a wide variety of cast parts that benefit from the corrosion and wear resistance characteristics provided by a zirconium oxide layer.

As FIG. 1 illustrates, a cast substrate is provided at step 120. In some examples, the substrate is a cast metal, near-shape part. The cast substrates may, in some examples, define cast medical implant parts made of a zirconium alloy, such as Zirconium-2.5 Niobium.

FIGS. 2-6 show two examples of such cast parts, femoral head 160 and femoral knee 180 (albeit in post-treated and oxidized conditions defining, respectively, femoral head oxidized layer 164 and femoral knee oxidized layer 184). Although FIGS. 2-6 provide two particular cast shapes to which the disclosed methods may be applied, the disclosed methods may include providing cast substrates different forms than those shown in FIGS. 2-6.

In some examples, the casts provided may have been cast to near-shape parts using centrifugal casting processes. Centrifugal casting may provide improved pre-treatment surface conditions compared to alternative casting methods. Centrifugally casted casts are not, however, required. In fact, disclosed methods may improve the surface quality of lower quality casts to cause the casts to adequately accept satisfactory zirconium oxide layers.

As FIG. 1 shows, the cast substrate is hot isostatic pressed at step 125. Hot isostatic pressing often includes placing the cast in a chamber surrounded by an inert fluid, which often is a gas. The inert gas applies a substantially even, predetermined pressure around the entire exposed surface of the part being pressed.

Applying pressure evenly effectively reduces the internal porosity of the cast part, improving the part's mechanical properties such as hardness, smoothness, and uniformity, retaining a substantially similar shape. Improving the part's mechanical properties may at least partially result from increasing the density of the cast part. Relative to a cast part that are not isostatically pressed, the higher density cast part has a reduced porosity and increased material integrity. The pressure applied may be adjusted by introducing or removing inert fluid to or from the chamber or by adjusting the temperature of the contained gas.

In some examples, the casts are isostatically pressed at step 125 at a pressure between 15,000 to 26,000 pounds per square inch. The inventor has observed that a target pressure of 25,000 psi has produced especially satisfactory results. However, any pressure between 15,000 and 26,000 psi has been observed to produce satisfactory cast parts with reduced internal porosity.

With regard to temperature, the casts may be isostatically pressed at step 125 at a temperature range of 1500 to 1700 degrees Fahrenheit. Hot isostatically pressing the cast part at 1,650° F. has been observed to produce excellent results.

In one example, the cast provided at step 120 is hot isostatically pressed at 25,000 is at 1,650° F. for a period of 2 hours. Timeframes of 1 to 2 hours at the temperatures and pressures described above are also suitable.

The temperature, pressure, and time parameter examples described above for the hot isostatic pressing step have been found to produce satisfactory results. Skilled technicians will recognize that various combinations of temperature, pressure, and time within the ranges described above will yield satisfactory results.

As FIG. 1 shows, the cast substrate is thermally treated at step 130. In some examples, thermally treating the cast substrate includes exposing the cast part to a temperature of 1,800 to 2,400 degrees Fahrenheit for a period of 1 to 5 hours. Exposing the cast to a temperature of over 2000 degrees Fahrenheit for two hours has been found to provide particularly satisfactory results.

Thermally treating the cast in this manner may produce, amongst other benefits, finer, more uniform grain boundaries proximate the surface of the cast and, in some cases, throughout the cast. The thermal treatment may, for example, encourage alloy elements and segregated elements at grain boundaries to diffuse within the cast and evenly redistribute throughout the cases internal material. As a result, thermal treating the cast may provide it with improved mechanical properties, such as improved toughness and ductility.

In some examples, thermally treating the cast substrate may include a rapid quench step. In this step, the cast is rapidly quenched at two bars of pressure within a lower-temperature quenching medium to rapidly reduce the temperature of the cast. The cast may, for example, be reduced from 2000 degrees Fahrenheit to below 200 degrees Fahrenheit a short period of time in a quenching medium that is 150 degrees Fahrenheit or less. In some examples, quenching the cast to reduce its temperature to 150 degrees Fahrenheit has been found to produce particularly satisfactory results.

Rapid quenching as described above has been observed to more quickly reduce atomic movement within the cast substrate thereby reducing the amount of time required to reset the cast's microstructure. Resetting the microstructure more quickly may result in finer, more uniform grain boundaries compared to ambient cooling.

As FIG. 1 illustrates, the cast substrate is machined at step 135. Machining the cast substrate at step 135 includes conforming the cast substrate to desired dimensions for the part after it is treated at step 125 or step 130. In some cases, step 125 and/or step 130 may introduce flaws in the cast's shape or size. Machining at step 135 may, for example, help correct any such introduced flaws.

As FIG. 1 shows, the surface of the cast substrate is treated to accept an oxide layer at step 140. In some examples, treating the surface of the cast substrate may include three sub-steps: polishing the cast substrate according to a first polishing process at step 143, peening the cast substrate at step 146, and polishing the cast substrate according to a second polishing process at step 149. The surface treatments applied at step 140 further improve surface characteristics of the cast to increase the likelihood of satisfactory oxidation at step 150.

As FIG. 1 illustrates, the cast substrate is polished according to a first polishing process at step 143. This first polishing process may include a vibratory finishing step, wherein one or more casts may be placed a container amongst polishing media, wherein the casts and the polishing media are tumbled relative one another. In some examples, this vibratory finishing step is repeated to perform a multi-stage vibratory finishing process, wherein the cast is tumbled within abrasive particle media of progressively smaller or of increasingly granularity at each stage.

In some examples, this multi-stage vibratory finishing process may include five stages. Examples of granularities used in such a five-stage process may include: A-80, A-30, A-16, A-6, and 2400 grit. In some examples, this vibratory finishing process may be referred to as "harperizing" performed according to "harperizing processes" known in the art.

As FIG. 1 shows, the cast substrate is peened at step 146. In some examples, peening the cast substrate includes repeatedly contacting the cast's surface with one or more articles of peening media to alter and refine the cast's surface's microstructure without altering the substrate material. Prior to peening casts' surfaces, the surfaces may define visible exterior grain boundaries, which may reduce the surfaces' ability to accept a satisfactory oxide layer. In some examples, peening improves the casts' surface characteristics and, in some examples, treats the surface to define visual and structural uniformities of equal or greater quality than forged parts.

In some examples, the cast is peened by repeatedly blasting spherical glass beads toward the cast's surface at approximately 100 pounds per square inch. Additionally or alternatively, steel beads, ceramic beads, and steel shot may be used as the peening media. In some examples, casts are sufficiently peened after repeatedly blasting peening media toward the cast substrate for up to five minutes. However, peening the surface for 30 seconds to 60 seconds has been found to provide satisfactory results in many cases.

By repeatedly blasting the cast's surface with the peening media, the surface layer of the cast is plastically deformed as a result of the compressive force applied by the peening media. This plastic deformation caused by the peening media's compressive force is substantially permanent, and thus should not return elastically to its original lattice microstructure (as often occurs with elastic deformation). This may result in a permanent change to the microstructure of the surface layer, effectively defining a "matte" or "blended-in" appearance of the grain boundaries that presents ell defined or visually indistinguishable lines.

As FIG. 1 illustrates, the cast substrate is polished according to a second polishing process, or a finishing process, at step 149. This second process includes a multi-stage vibratory polishing step substantially similar to the one performed at step 143. The second polishing process, however, additionally or alternatively may include a final grinding step.

In the final grinding step, a fine polishing compound is applied to the cast's surface via a contacting-type grinding machine. In some examples, this contacting-type grinding machine applies the polishing compound to the cast's surface to remove from 0.001 to 0.002 inches of thickness from the surface, resulting in substantially smooth, bright surfaces that define a reduced number of scratches and visible grain boundary lines. In some examples, "finishing the peened surface" may be accomplished by performing the multi-stage vibratory polishing step, the final grinding step, or both of these steps.

Upon polishing the cast substrate according to the second polishing or finishing process at step 149, the cast substrate has been prepared for oxidation. As a result, some of the disclosed methods may end at this step. For example, many manufacturers may desire to simply produce cast parts treated to accept oxidation without performing an active oxidation step. Similarly, this disclosure notes that the improvements in surface properties provided by the foregoing steps, independently or cooperatively, may reduce apparent grain boundaries and produce substantially smooth, dense, and uniform cast products with low friction coefficients, which may be beneficial without an further oxidation process.

As FIG. 1 shows, the surface of the cast substrate is oxidized at step 150. At this step, the treated surface of a cast accepts an oxide layer defining a thin, transparent oxygen rich film. These natural films, particularly at thicknesses of 2-10 microns, provide hard, uniform, smooth, and dense surfaces, particularly in examples wherein cast substrates define zirconium alloy parts treated according to the disclosed methods. The oxide layers provide many of the desired surface characteristics discussed above, which may be particularly useful with medical implants. Additionally or alternatively, transparent, natural films often produce bright metallic appearances, which may, in some examples, appear blue-black or black in color.

In various examples, oxidizing the surface of the cast substrate may be accomplished either actively or passively, or a combination thereof. Zirconium-2.5 niobium, for example, oxidizes when exposed to air, with or without further intervention. However, cast substrates may be exposed to heat for a predetermined length of tame to accelerate the oxidization process, which may produce harder, smoother, an more uniform oxidized layers in reduced time compared to passively oxidizing a cast substrate. Heating zirconium niobium casts to 600-1500 degrees Fahrenheit in an oxidative environment for a period of 2-6 hours has been found to produce particularly satisfactory results.

The resultant oxidized casts often present a blue-black or black visual appearance and lack visible grain boundary lines. In some examples, the appearance may be similar to (or even indistinguishable from) oxidized wrought or forged zirconium-2.5 niobium medical implants. Further, the resultant oxidized casts define surface characteristics, such as low friction coefficients, increased hardness, and resistance to wear and corrosion, that may equal or exceed those of wrought or forged oxidized zirconium-2.5 niobium medical implants.

Figure 2:
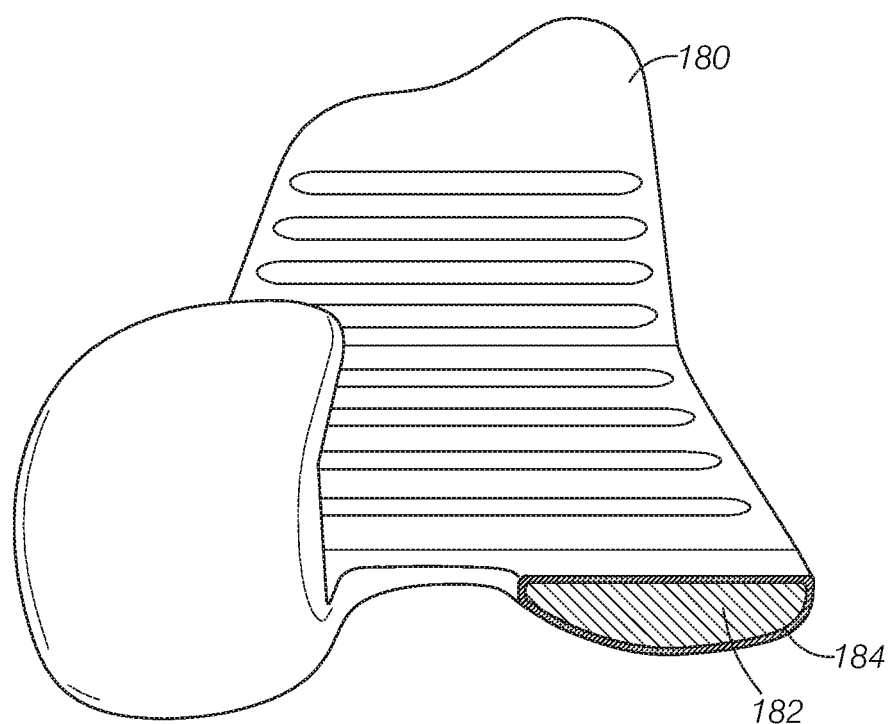
FIG. 2 is bottom perspective view of a first example of a cast zirconium alloy substrate defining a knee replacement femoral component with a portion removed to show internal structure.
Figure 3:
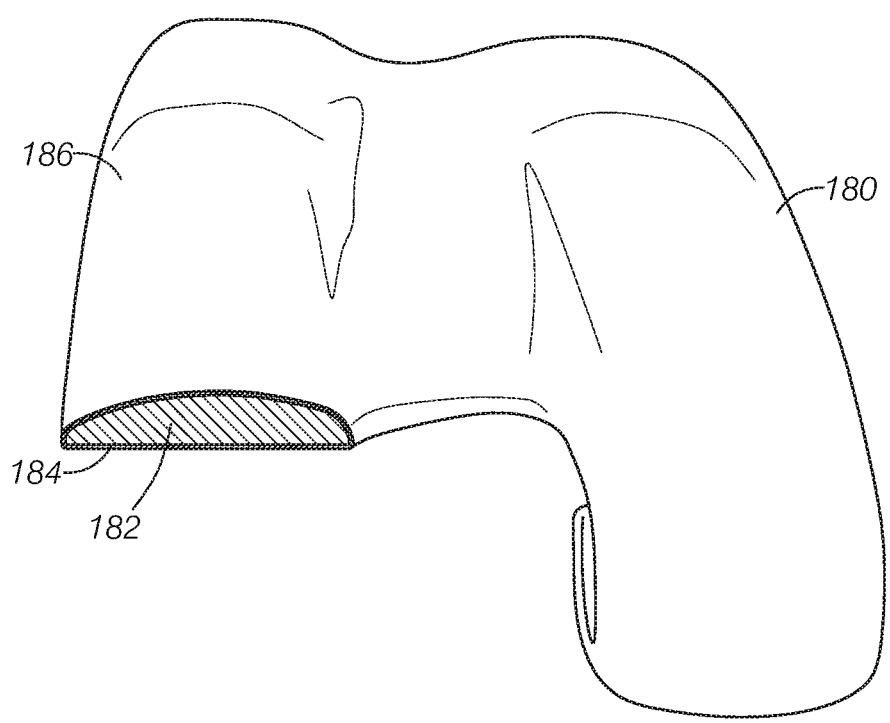
FIG. 3 is a top perspective view of the knee replacement femoral component shown in FIG. 2.
Figure 4:
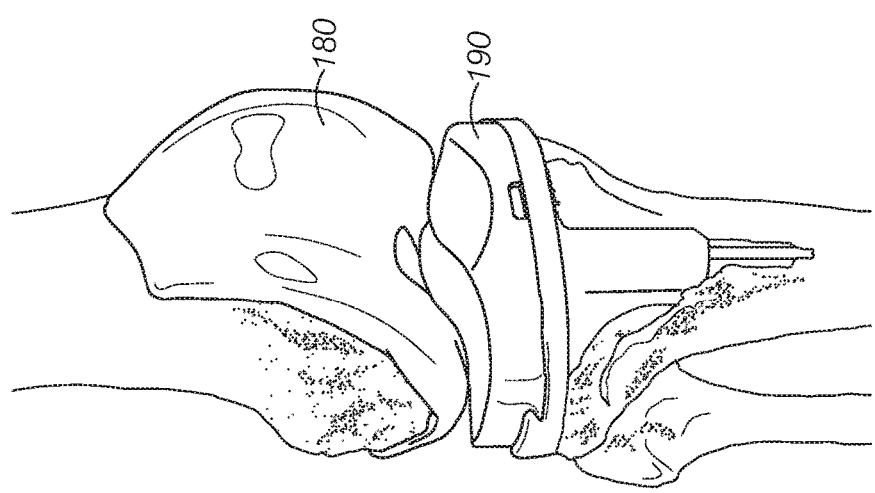
FIG. 4 is a perspective view of the knee replacement femoral component shown in FIG. 2 in use in a patient as a replacement knee component.

FIGS. 2-6 provide two examples of cast parts that have been treated and oxidized according to disclosed methods: femoral head 160 and femoral knee 180. As FIG. 2 shows, femoral knee 180 defines femoral knee oxidized layer 184 surrounding an internal zirconium oxide layer 182, which provides desired surface characteristics to femoral knee 180. For example, femoral knee 180's upper surface 186 defines a blue-black metallic sheen (though the color is not readily displayed in the figure) that defines a substantially hard, smooth, uniform shape. As FIG. 4 shows, femoral knee 180 is appropriately shaped to serve as a knee replacement femoral element, wherein upper surface 186 is configured to articulate against a paired knee member 190.

Figure 5:
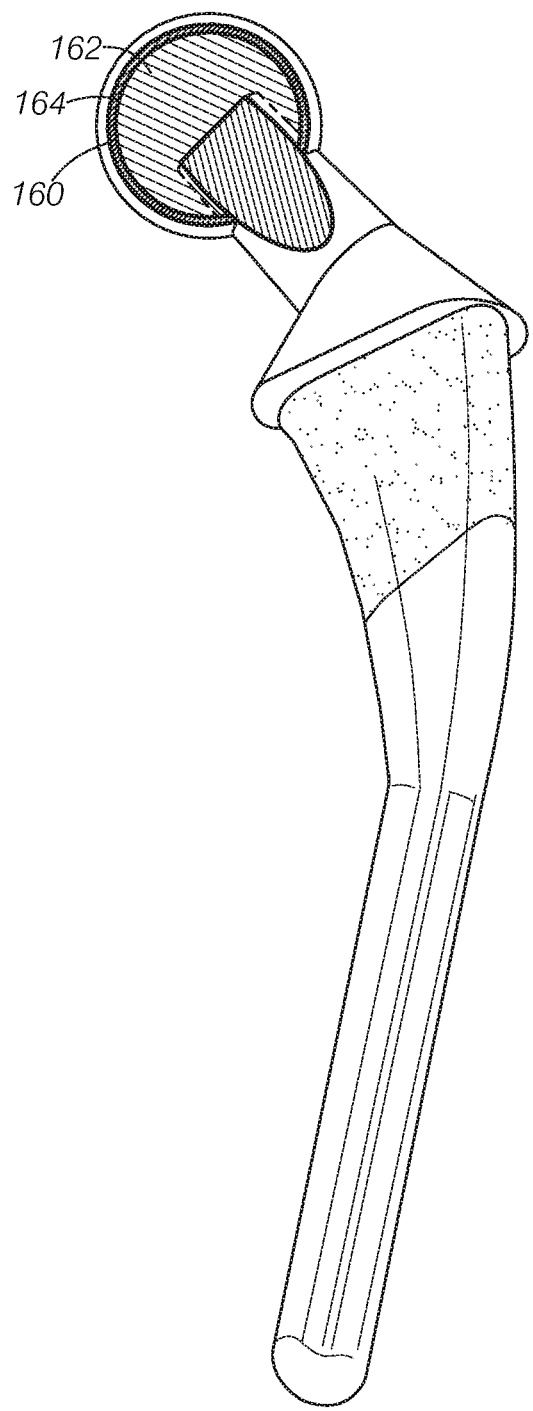
FIG. 5 is a perspective view of a second example of a cast zirconium alloy substrate defining a hip replacement femoral head with a portion removed to show internal structure.
Figure 6:
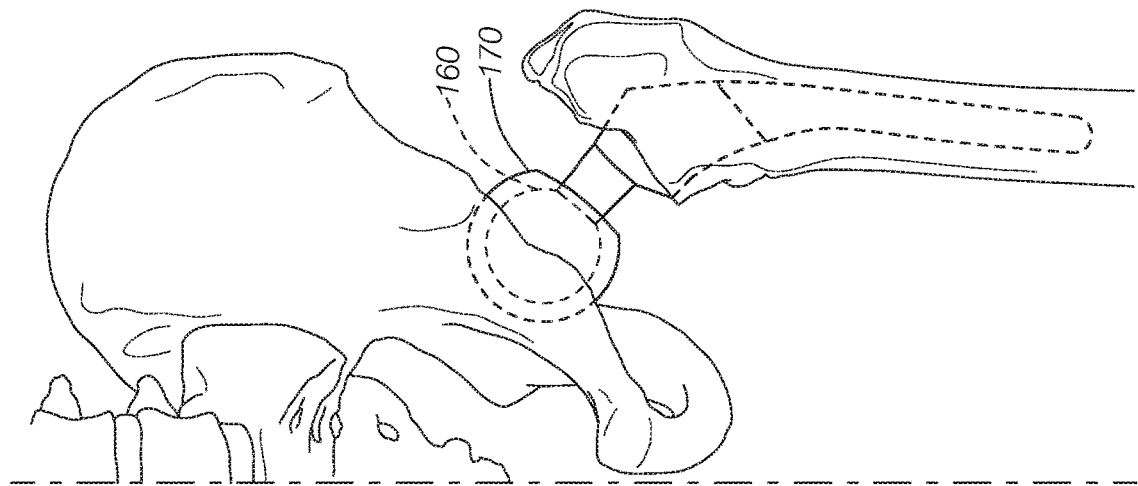
FIG. 6 is a perspective view of the hip replacement femoral head in use in a patient as a replacement hip.

As FIG. 5 shows, femoral head 160 similarly defines femoral head oxidized layer 164 enclosing an internal zirconium oxide layer 162. Similar to femoral knee oxidized layer 184, femoral head oxidized layer 164 is configured to articulate within a femoral head receiving member 170 when implanted in hip replacement, illustrating the importance of femoral head oxidized layer 164's smooth, uniform, low friction design. Although not discussed at length, this disclosure contemplates paired knee members, similar to paired knee member 190, and femoral head receiving members, such as femoral head receiving member 170, being cast, treated, and oxidized according to disclosed methods additionally or alternatively to the femoral heads and knees. In other examples, however, paired knee members and femoral head receiving members may be constructed out of a soft plastic.

Figure 7:
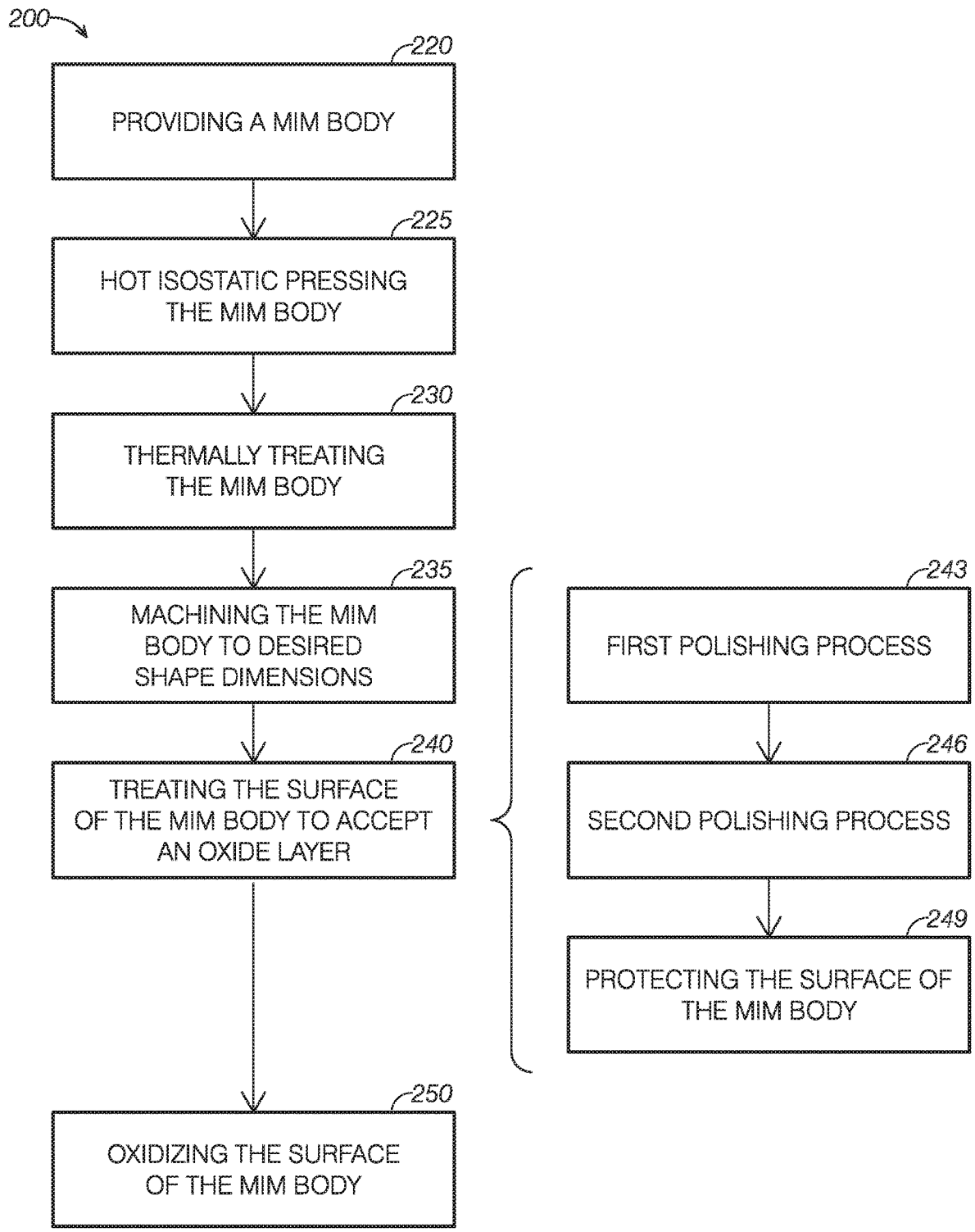
FIG. 7 is a flow diagram depicting a method of forming an oxide layer on a metal body, wherein the metal body is produced via Metal Injection Molding (MIM).

Turning now to FIG. 7, a flow diagram depicting a method 200 of forming an oxide layer on a metal body is shown. In some embodiments, the metal body may be produced via Metal Injection Molding (MIM). Method 200 includes many similar or identical steps to Method 100. Thus, for the sake of brevity, each step of method 200 will not be redundantly explained. Rather, key distinctions between method 200 and method 100 will be described in detail and the reader should reference the discussion above, for features substantially similar between the two methods.

As shown in FIG. 7, method 200 may include the steps of providing 220 a MIM (Metal Injection Molded) body; hot isostatic pressing 225 the MINI body, heat treating 230 the MIM body, machining 235 the MIM body to desired shape dimensions, treating 240 the surface of the MIM body; and oxidizing 250 the surface of the MIM body. Treating 240 the surface of the MINI body may include a first polishing step 243, and second polishing step 246 and protecting 249 the surface of the MIM body prior to oxidizing the surface.

The treating the surface step 240 may include any of the steps described above with respect to surface treatment step 140. For example, the surface treatment step may include multistage vibratory finishing process. In some embodiments, the MIM body may be processed via particle media that is increasingly fine at each stage. For example, the MIM body may be tumbled in particle media that is increasingly fine at each stage.

As shown in FIG. 7, in some embodiments, the surface treatments step may include a first polishing step 243, and second polishing step 246. In some embodiments, the first polishing step 243 may be a first vibratory finishing step. In some embodiments, the second polishing step may a second vibratory finishing step. In some embodiments, at least one of the first and second vibrator finishing steps comprises a Harperizing process. Furthermore, in some embodiments, at least one of the first and second vibratory finishing steps comprises a multi-stage vibratory finishing process.

The MIM body may be produced via Metal Injection Molding (MIM). Metal Injection Molding the MIM body may include mixing a feedstock comprising one or more metal powders and one or more binders. The feedstock may then be injected into a mold to produce a "green part" of near shape dimensions. The resulting green part may be removed from the mold.

In some embodiments, the green part may then be placed in a second mold. A second feedstock comprising one or more metal powders and one or more binders may be mixed. The second feedstock may then be injected into the second mold, thereby forming a dual composition green part having an over-molded portion made up of the second feedstock and a base portion made up of the first feedstock.

At least some of the binders, may then be removed, for example by submerging the green part in a solvent bath. Next the green part may be sintered, thereby sintering the metal powder(s) together to form the MIM body. In this regard, MIM bodies comprising a base portion of a first material and an over-molded portion of a second material may be produced. As can be appreciated, a MIM body comprising a second over-molded portion of a third material could also be produced via a third mixing/molding step. The MIM body may then be processed as described above with respect to method 200.

As described above zirconium alloys may be particularly well suited to the disclosed oxidation layer formation processes. Thus, in some embodiments, the first MIM body may comprise a zirconium alloy. For example, the MIM body may comprise a zirconium-niobium alloy, such as zirconium-2.5 niobium, among others.

As described above, in some embodiments, the MIM body may have a dual composition, e.g., a base portion of a first material and an over-molded portion of a second material. In some embodiments, the base portion may comprise a titanium alloy. For example, the base portion may comprise a Ti-6Al-4V alloy base. In some embodiments, the over-molded portion may comprise any of the zirconium alloys described above.

As described above, the MIM body may be hot isostatic pressed 225. In one embodiment, the Metal Injection Molded body may be hot isostatic pressed at a pressure range of 15,000 pounds per square inch to 26,000 pounds per square inch. In some embodiments, the Metal Injection Molded body may be hot isostatic pressed at a temperature of 1,500 degrees Fahrenheit to 1,700 degrees Fahrenheit for a period of one to four hours.

As described above, the MIM body may be heat treated 230. In some embodiments, the heat treating step 230 may comprise heating the Metal Injection Molded body to 1,800 degrees Fahrenheit to 2,400 degrees Fahrenheit for a period of one to five hours.

As described above, the surface of the MIM body may be oxidized 250. In some embodiments, the oxidizing step may include heating the substrate to 600 to 1,500° F. in an oxidative environment for 2 to 6 hours. In some embodiments, the oxidizing step may include forming a zirconium oxide surface layer having a thickness of 2 to 10 microns.

In some embodiments after the oxidizing step 250, the oxidized surface may then be mechanically finished. In some embodiments, the mechanically finishing step may comprise grinding the oxidized surface to remove up to 0.002 of surface material.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A method of forming an oxide layer on a surface of a Metal Injection Molded body, wherein the surface comprises a zirconium alloy, the method comprising:
   hot isostatic pressing the Metal Injection Molded body;
   heat treating the Metal Injection Molded body;
   machining the Metal Injection Molded body to desired shape dimensions;
   polishing the surface of the Metal Injection Molded body, wherein the polishing comprises:
      a first vibratory finishing step; and
      a second vibratory finishing step; and
   oxidizing the polished surface of the Metal Injection Molded body,
   wherein the Metal Injection Molded body comprises a base portion and an over-molded portion, wherein the base portion is a titanium alloy and the over-molded portion is the zirconium alloy.

2. The method of claim 1, wherein the Metal Injection Molded body is hot isostatic pressed at a pressure range of 15,000 pounds per square inch to 26,000 pounds per square inch at a temperature of 1,500 degrees Fahrenheit to 1,700 degrees Fahrenheit for a period of one to four hours.

3. The method of claim 1, wherein heat treating the Metal Injection Molded body includes heating the body to 1,800 degrees Fahrenheit to 2,400 degrees Fahrenheit for a period of one to five hours.

4. The method of claim 1, wherein the zirconium alloy comprises a zirconium-niobium alloy.

5. The method of claim 1, wherein the zirconium alloy is zirconium-2.5 niobium.

6. The method of claim 1, wherein oxidizing the polished surface includes forming a zirconium oxide surface layer having a thickness of 2 to 10 microns.

7. The method of claim 1, wherein oxidizing the polished surface includes heating the Metal Injection Molded body to 600 to 1,500° F. in an oxidative environment for 2 to 6 hours.

8. The method of claim 1, further comprising mechanically finishing the oxidized surface.

9. The method of claim 1, wherein mechanically finishing the oxidized surface includes grinding to remove up to 0.002" of surface material.

10. The method of claim 1, wherein at least one of the first and second vibratory finishing steps comprises a Harperizing process.

11. The method of claim 1, wherein at least one of the first and second vibratory finishing steps comprises a multi-stage vibratory finishing process.

12. A method of forming an oxide layer on a surface of a Metal Injection Molded body, wherein the surface comprises a zirconium alloy, the method comprising:
   hot isostatic pressing the Metal Injection Molded body;
   heat treating the Metal Injection Molded body;
   machining the Metal Injection Molded body to desired shape dimensions;
   polishing the surface of the Metal Injection Molded body, wherein the polishing is performed in a series of at least two steps; and wherein each successive step uses progressively smaller polishing particle media; and
   oxidizing the polished surface of the Metal Injection Molded body,
   wherein the Metal Injection Molded body comprises a base portion and an over-molded portion, wherein the base portion is a titanium alloy and the over-molded portion is the zirconium alloy.

13. The method of claim 12, wherein the polishing step comprises a multistage vibratory finishing process.

14. The method of claim 13, wherein the multi-stage vibratory finishing comprises a five stage vibratory finishing process.

15. The method of claim 13, wherein at least one stage of the multistage vibratory finishing process comprises a Harperizing process.

16. The method of claim 12, wherein the zirconium alloy is zirconium-2.5 niobium.

17. The method of claim 12, further comprising mechanically finishing the oxidized surface.

\* \* \* \* \*